United States Patent
Kim et al.

(10) Patent No.: US 12,247,082 B2
(45) Date of Patent: Mar. 11, 2025

(54) HIGHLY EFFICIENT ANTI-TFPI ANTIBODY COMPOSITION

(71) Applicant: GREEN CROSS CORPORATION, Yongin-si (KR)

(72) Inventors: Min Jung Kim, Yongin-si (KR); Geun Hye Yeo, Yongin-si (KR); Haeng Eun Song, Yongin-si (KR); Ji Yoon Park, Yongin-si (KR); Yuna Kim, Yongin-si (KR)

(73) Assignee: GREEN CROSS CORPORATION, Yongin (KR)

( * ) Notice: Subject to any disclaimer, the term of this patent is extended or adjusted under 35 U.S.C. 154(b) by 1031 days.

(21) Appl. No.: 17/276,276

(22) PCT Filed: Sep. 6, 2019

(86) PCT No.: PCT/KR2019/011582
§ 371 (c)(1),
(2) Date: Mar. 15, 2021

(87) PCT Pub. No.: WO2020/060087
PCT Pub. Date: Mar. 26, 2020

(65) Prior Publication Data
US 2022/0025067 A1    Jan. 27, 2022

(30) Foreign Application Priority Data
Sep. 21, 2018    (KR) .................. 10-2018-0113974

(51) Int. Cl.
| C07K 16/28 | (2006.01) |
| C07K 1/16 | (2006.01) |
| C07K 1/22 | (2006.01) |
| C07K 1/34 | (2006.01) |
| C07K 1/36 | (2006.01) |
| C07K 16/38 | (2006.01) |

(52) U.S. Cl.
CPC .............. *C07K 16/38* (2013.01); *C07K 1/165* (2013.01); *C07K 1/22* (2013.01); *C07K 1/34* (2013.01); *C07K 1/36* (2013.01); *C07K 2317/10* (2013.01); *C07K 2317/92* (2013.01)

(58) Field of Classification Search
CPC ........... C07K 1/165; C07K 1/22; C07K 1/34; C07K 1/36; C07K 2317/10; C07K 2317/92; C07K 16/065; A61K 39/395
See application file for complete search history.

(56) References Cited

U.S. PATENT DOCUMENTS

| 10,125,189 | B2 * | 11/2018 | Teschner ................. A61P 37/00 |
| 2008/0312425 | A1 | 12/2008 | Bonnerjea et al. |
| 2010/0135987 | A1 | 6/2010 | Hickman et al. |
| 2012/0028901 | A1 | 2/2012 | Dockal et al. |
| 2012/0108796 | A1 * | 5/2012 | Wang ........................ A61P 7/04 |
| | | | 530/388.15 |
| 2016/0115195 | A1 * | 4/2016 | Mendiratta .......... C07K 16/241 |
| | | | 530/387.3 |
| 2016/0326253 | A1 * | 11/2016 | Ueda ....................... C07K 1/18 |
| 2017/0073428 | A1 * | 3/2017 | Pittman .............. A61K 39/3955 |
| 2017/0306036 | A1 * | 10/2017 | Vu ..................... C07K 16/2878 |

FOREIGN PATENT DOCUMENTS

| JP | 2012-506383 A | 3/2012 |
| JP | 2013-531623 A | 8/2013 |
| JP | 2015-528464 A | 9/2015 |
| JP | 2016-519137 A | 6/2016 |
| KR | 10-2015-0027807 A | 3/2015 |
| KR | 10-2016-0102283 A | 8/2016 |
| KR | 10-2016-0103767 A | 9/2016 |
| WO | 2010/072691 A1 | 7/2010 |
| WO | 2011/104381 A2 | 9/2011 |
| WO | 2011/146179 A2 | 11/2011 |
| WO | 2011/147921 A1 | 12/2011 |
| WO | 2014/036071 A1 | 3/2014 |
| WO | 2014/180852 A1 | 11/2014 |
| WO | WO-2015070068 A1 * | 5/2015 | ........... A61K 39/395 |
| WO | WO-2016137108 A1 * | 9/2016 | ........... A61K 39/395 |
| WO | 2017/117490 A1 | 7/2017 |

OTHER PUBLICATIONS

Renee Boerner et al., "Defining Your Product Profile and Maintaining Control Over It, Part 3", BioProcess International, Oct. 2005, 3: pp. 50-56.
Chris Bailey-Kellogg et al., "CHOPPI: A Web Tool for the Analysis of Immunogenicity Risk from Host Cell Proteins in CHO-Based Protein Production", Biotechnology and Bioengineering, Nov. 2014, vol. 111, No. 11, pp. 2170-2182.
Anne S. De Groot et al., "Reducing risk, improving outcomes: bioengineering less immunogenic protein therapeutics", Clinical Immunology, Mar. 6, 2009, 131(2), pp. 189-201.
Peng Wang et al., "A Systematic Assessment of MHC Class II Peptide Binding Predictions and Evaluation of a Consensus Approach", PLoS Computational Biology, Apr. 4, 2008, e1000048, 11 pages, vol. 4, Issue 4.
Robert L. Fahrner et al., "Industrial Purification of Pharmaceutical Antibodies: Development, Operation, and Validation of Chromatography Processes", Biotechnology and Genetic Engineering Reviews, Jul. 2001, pp. 301-327, 18(1).
Koran Office Action of KR10-2018-0113974 dated Feb. 12, 2020.
Koran Office Action of KR10-2018-0113974 dated Oct. 30, 2020.

(Continued)

*Primary Examiner* — Hong Sang
(74) *Attorney, Agent, or Firm* — Sughrue Mion, PLLC (57) ABSTRACT

The present disclosure relates to a pharmaceutical highly efficient anti-TFPI antibody composition including an anti-TFPI antibody for treating hemophilia, in which the content of HCP in a drug substance is less than 10.0 ng/mg, and the content of LPA in the drug substance or the drug product is less than 1.0 ng/mg. According to the present disclosure, a highly efficient anti-TFPI antibody composition having very low contents of HCP and LPA may be provided by providing a separation/purification process capable of minimizing anti-TFPI antibody polymer generation, and may be effectively used for the treatment of antibody-induced hemophilia patients and for the prevention of blood coagulation disease.

8 Claims, 4 Drawing Sheets

(56) References Cited

OTHER PUBLICATIONS

International Search Report of PCT/KR2019/011582 dated Dec. 20, 2019 [PCT/ISA/210].
Pete Gagnon et al., "Transient conformational modification of immunoglobulin G during purification by protein A affinity chromatography", Journal of Chromatography A, 2015, vol. 1395, pp. 136-142 (7 pages).
Abhinav A. Shukla et al., "Downstream processing of monoclonal antibodies—Application of platform approaches", Journal of Chromatography B, 2007, vol. 848, pp. 28-39 (12 pages total).
Hui F. Liu et al., "Recovery and purification process development for monoclonal antibody production", MABS, 2010, vol. 2, No. 5, pp. 480-499 (20 pages total).
Ida Hilden et al., "Hemostatic effect of a monoclonal antibody mAb 2021 blocking the interaction between FXa and TFPI in a rabbit hemophilia model", Blood, Jun. 14, 2012, vol. 119, No. 24, pp. 5871-5878 (8 pages).
Communication dated May 29, 2024, issued in Canadian Application No. 3,111,179.

\* cited by examiner

HIGHLY EFFICIENT ANTI-TFPI ANTIBODY COMPOSITION

CROSS REFERENCE TO RELATED APPLICATIONS

This application is a National Stage of International Application No. PCT/KR2019/011582 filed on Sep. 6, 2019, claiming priority based on Korean Patent Application No. 10-2018-0113974 filed on Sep. 21, 2018.

TECHNICAL FIELD

The present disclosure relates to a highly efficient anti-TFPI antibody composition for treating hemophilia.

BACKGROUND ART

Anti-TFPI antibody is an anti-tissue factor pathway inhibitor (hereinafter referred to as anti-TFPI) recombinant antibody which is a human IgG4 monoclonal antibody having a high affinity for tissue factor pathway inhibitor (hereinafter referred to as TFPI).

The anti-TFPI antibody is used as a hemophilia therapeutic agent which coagulates blood by inhibiting the binding between TFPI and activated factor X (FXa) and inducing activation of the downstream blood coagulation factor FX in the extrinsic blood coagulation pathway.

The anti-TFPI antibody is an IgG4 type antibody, and when it is applied to a general antibody production process, problems arise in that polymer generation during the process increases, resulting in a decrease in the therapeutic effect of the product, and the reproducibility of the process is low due to the high instability of the antibody at low pH values.

In particular, when a polymer is present in the final anti-TFPI antibody concentrate at an appropriate level or higher, the polymer has adverse effects in that it reduces the binding affinity of the anti-TFPI antibody for the antigen TFPI, resulting in a decrease in the efficacy of the antibody.

Hence, process conditions should be appropriately maintained so as to prevent the generation of the polymer in the anti-TFPI antibody production process, and the polymer inevitably generated in the antibody purification process should be selectively removed.

Thus, developing a process for purifying a high-purity anti-TFPI antibody is necessarily required for the development of a highly efficient anti-TFPI antibody therapeutic agent.

Thus, in order to produce a highly efficient anti-TFPI antibody composition, the present inventors have conducted studies on conditions for a neutralization process in an affinity chromatography process for adsorbing protein impurities, a process for minimizing the generation of an anti-TFPI antibody polymer and selectively removing the generated polymer in a mixed-mode chromatography purification process, and a process for maximizing the anti-TFPI antibody purification yield in a first ultrafiltration and diafiltration process, a second ultrafiltration and diafiltration process and a final concentration process, and have found that a highly efficient anti-TFPI antibody can be produced, thereby completing the present disclosure.

PRIOR ART DOCUMENTS

Patent Documents (Patent Document 1) Korean Patent No. 10-1744899
(Patent Document 2) Korean Patent No. 10-1804988

Non-Patent Documents (Non-Patent Document 1) 1. Defining your product profile and maintaining control over it, part 2: challenges of monitoring host cell protein impurities. BioProcess Int 2005; 3:52-4, 6, 8
(Non-Patent Document 2) 2. CHOPPI: A Web Tool for the Analysis of Immunogenicity Risk from Host Cell Proteins in CHO-Based Protein Production. Biotechnol Bioeng. 2014 November; 111(11): 2170-2182.
(Non-Patent Document 3) 3. Reducing risk, improving outcomes: bioengineering less immunogenic protein therapeutics. Clin Immunol. 2009 May; 131(2):189-201
(Non-Patent Document 4) 4. A systematic assessment of MHC class II peptide binding predictions and evaluation of a consensus approach. PLoS Comput Biol. 2008 Apr. 4; 4(4):e1000048.

DISCLOSURE OF INVENTION

Technical Problem

It is an object of the present disclosure to provide a highly efficient anti-TFPI antibody composition having very low contents of HCP and LPA by (i) minimizing polymer generation by introducing a neutralization process after a low-pH affinity chromatography elution process in order to increase antibody stability in an affinity chromatography process, (ii) determining polymer separation conditions by selecting an efficient purification resin in order to selectively remove a polymer contained in the anti-TFPI antibody in a mixed-mode chromatography process, and (iii) maximizing the anti-TFPI antibody purification yield while minimizing the formation of the anti-TFPI antibody polymer in a final concentration process, in order to produce a highly efficient anti-TFPI antibody composition.

The technical problems of the present disclosure are not limited to the above-mentioned technical problems, and other technical problems which are not mentioned may be clearly understood by those skilled in the art from the following description.

Solution to Problem

To achieve the above object, the present disclosure provides a pharmaceutical highly efficient anti-TFPI antibody composition including an anti-TFPI antibody for treating hemophilia, in which the total content of HCP and LPA in a drug substance is 10 ng/mg or less.

HCP (host cell protein) is a unique protein found in a CHO cell which is used as a host in anti-TFPI antibody production, and the content of HCP in the cell culture is extremely as high as about 500,000 ng/mg. On the other hand, LPA (leachable protein A) is a protein A impurity dissociated from a resin in a purification process, and the content thereof may differ between products depending on purification conditions, but is generally about 10 ng/mg. Thus, the content of the HCP impurity is relatively higher than the content of the LPA impurity, and it is essential and very important to lower the contents of HCP and LPA in order for an anti-TFPI antibody composition to be effective.

If the content of HCP in the anti-TFPI antibody composition is maintained at less than 10.0 ng/mg and the content of LPA in the composition is maintained at less than 1.0 ng/mg, when the composition is administered as a therapeutic drug to the human body, it has an excellent property of lowering immunogenic side effects, and thus may exhibit an excellent effect as an anti-TFPI antibody composition.

In one embodiment of the present disclosure, the total content of HCP and LPA may be 5 ng/mg or less.

If the total content of HCP and LPA in the anti-TFPI antibody composition is maintained at 5 ng/mg or less, when the composition is administered as a therapeutic drug to the human body, it has an excellent property of lowering immunogenic side effects, and thus may exhibit an excellent effect as an anti-TFPI antibody composition.

In another embodiment of the present disclosure, the highly efficient anti-TFPI antibody composition may be produced through a process of clarifying a culture containing anti-TFPI, an affinity chromatography process, a viral inactivation process, a first ultrafiltration and diafiltration process, a mixed-mode chromatography process, a nanofiltration process, and a final concentration process.

In still another embodiment of the present disclosure, a second ultrafiltration and diafiltration process may further be included after the mixed-mode chromatography process.

In yet another embodiment of the present disclosure, the mixed-mode chromatography process may remove 98% or more of a polymer of the anti-TFPI antibody by performing two or more plural mixed-mode chromatography processes using different types of column resin.

If 98% or more of the polymer is removed, when the composition is administered as a therapeutic drug to the human body, it has the advantages of lowering immunogenic side effects and increasing the binding affinity of the anti-TFPI antibody to TFPI, and thus may exhibit better activity as an anti-TFPI antibody composition.

In yet another embodiment of the present disclosure, the affinity chromatography process may include the steps of: neutralizing an eluate, which passed through an affinity chromatography column, in the range of pH 4.0 to 6.0; and leaving the neutralized eluate to stand at room temperature (15 to 25° C.) for 8 to 16 hours.

In yet another embodiment of the present disclosure, the concentration process may include a rinse solution circulation/recovery process.

In yet another embodiment of the present disclosure, the content of the anti-TFPI antibody polymer in the drug substance may be less than 1%.

In yet another embodiment of the present disclosure, the drug substance may have an $EC_{50}$ value of 3.26 ng/mL or less.

When the $EC_{50}$ value of the drug substance is 3.26 ng/mL or less, the composition has the advantages of increasing the binding affinity of the anti-TFPI antibody for TFPI and improving the ability of the anti-TFPI antibody to neutralize the function of TFPI, and thus may exhibit an excellent effect as an anti-TFPI antibody composition.

In yet another embodiment of the present disclosure, a high-purity anti-TFPI antibody composition may be produced, in which the content of HCP in the drug substance is less than 10.0 ng/mg and the content of LPA in the drug substance is less than 1.0 ng/mg, and at the same time, the content of HCP per unit content of the anti-TFPI antibody in the drug substance which is a final product is at least 10,000-fold lower than the content of HCP per unit content of the anti-TFPI antibody in a clarified culture which is a starting material.

If the anti-TFPI antibody composition is maintained as a high-purity anti-TFPI antibody composition in which the content of HCP in the drug substance is less than 10.0 ng/mg and the content of LPA in the drug substance is less than 1.0 ng/mg, and at the same time, the content of HCP per unit content of the anti-TFPI antibody in the drug substance subjected to the purification process is at least 50,000-fold lower than the content of HCP per unit content of the anti-TFPI antibody in the clarified culture, when the anti-TFPI antibody composition is administered as a therapeutic drug to the human body, it has the advantage of lowering immunogenic side effects, and thus may exhibit better activity as an anti-TFPI antibody composition.

In yet another embodiment of the present disclosure, the content of HCP in the drug substance may be less than 10.0 ng/mg and the content of LPA in the drug substance may be less than 1.0 ng/mg, and at the same time, the binding activity $EC_{50}$ value of the drug substance may be 3.26 ng/mL or less.

If the total content of HCP and LPA is 5.0 ng/mg or less while the binding activity $EC_{50}$ value is 3.26 ng/mL or less, when the antibody composition is administered as a therapeutic drug to the human body, it has the advantages of lowering immunogenic side effects and increasing the binding affinity of the anti-TFPI antibody for TFPI, and thus may exhibit better activity as an anti-TFPI antibody composition.

Advantageous Effects of Invention

According to the present disclosure, a highly efficient anti-TFPI antibody composition having very low contents of HCP and LPA is provided by minimizing polymer generation, effectively removing the generated polymer, and recycling a rinse solution in the concentration process, thus maximizing the purification yield. Thus, the highly efficient anti-TFPI antibody composition may be effectively used for the treatment of antibody-induced hemophilia patients and for the prevention of blood coagulation disease.

MODE FOR THE INVENTION

A highly efficient anti-TFPI antibody composition of the present disclosure may be produced by an optimized method as described below. However, the present disclosure is not interpreted as being limited to embodiments of the present disclosure, and optimum conditions may change with changes in process conditions.

1. Culture Harvest and Clarification

A culture harvest and clarification process is intended to remove the cells and cell debris contained in a culture. This process was performed at 15 to 25° C.

First, a POD holder was equipped with a POD filter in order, and then the handle of the holder was turned to prevent leakage of liquid to portions other than the inlet and the outlet, and the filter was flushed with 200 to 300 L of water for injection.

Thereafter, a culture clarification buffer was passed to wash the POD filter mounted in the holder and a sterile capsule filter connected to the outlet. A culture harvest valve was opened to initiate culture clarification, and the pressure of the POD filter system was adjusted to not exceed 29 psi (2 bar) during culture clarification.

After completion of the culture clarification as described above, post-washing was performed with culture clarification buffer. After completion of the post-washing, a container containing the clarified culture collected therein was weighed and used in the next process. The process parameters and QA/PA (quality/performance attributes) of the culture harvest and clarification process are shown in Table 1 below.

TABLE 1

| Unit process | Process parameters | Operating ranges |
|---|---|---|
| Culture harvest and clarification | Inlet pressure (bar) during clarification | ≤2 |
| | Operating temperature (° C.) | 20 ± 5 |

| Unit process | QA/PA | Results |
|---|---|---|
| Culture harvest and clarification | Protein content (mg/mL) | 0.585 |
| | HCP content (ng/mg) | 559435.9 |
| | Binding activity potency $EC_{50}$ value (ng/mL) | 3.91 |

2. Affinity Chromatography

An affinity chromatography process is intended to adsorb and recover the anti-TFPI antibody composition from the culture. This process was performed using Mabselect sure resin at 15 to 25° C., but is not limited thereto, conventional Protein A resin may also be used.

First, packing evaluation was performed using an AKTA purification system to confirm suitability. In addition, CIP solution was flushed for 15 minutes, and then sanitization was performed with column wash buffer.

After equilibration was performed with equilibration buffer, the clarified culture was connected and adsorbed, and a sample that passed through the column was collected as an unbound solution. After completion of the adsorption, re-equilibration was performed by flushing with equilibration buffer. At this time, a re-equilibration solution that passed through the column was collected together with the unbound solution. After completion of the re-equilibration process, the column was washed with wash buffer, and a wash solution that passed through the column was collected.

In an elution process, the column was flushed with affinity chromatography elution buffer, and the eluate was collected from a time point at which it reached 0.8 times the gel volume. The eluate collected as described above was neutralized by adjusting the pH to 4.0 to 6.0 with a pH adjusting solution, and the neutralized eluate was stored at 15 to 25° C. until the next process. After completion of the process, column washing was performed while the resin was flushed with column wash buffer. Column CIP was performed with CIP buffer for 15 minutes, and the pH of the column was stabilized with equilibration buffer. Thereafter, the column was filled by flushing with gel storage solution, and then separated from the system and stored.

The process parameters and QA/PA of the affinity chromatography process are shown in Table 2 below.

TABLE 2

| Unit process | Process parameters | Operating conditions | |
|---|---|---|---|
| Affinity chromatography | Sample load (g/L of resin) | 20 ± 10 | |
| | Wash buffer load (CV) | 12 ± 6 | |
| | Elution buffer (pH) | 3.4 ± 0.4 | |
| | Eluate collection condition | Collected from a time point at which 0.8 CV of gel volume is reached | |
| | pH for eluate neutralization | 5.0 ± 1.0 | |

| | | Results | |
|---|---|---|---|
| Unit process | QA/PA | Eluate | Neutralized eluate |
| Affinity chromatography | Yield (%) | 103.8 | 102.8 |
| | Purity (monomer %) | 98.3 | 98.3 |
| | HCP (LRV) | 2.2 | 0.3 |
| | HCP content (ng/mg) | 3601.3 | 1857.8 |
| | LPA content (ng/mg) | 3.7 | 2.5 |
| | Endotoxin (EU/mg) | 0.13 | 0.10 |

3. Viral Inactivation

A viral inactivation process is intended to inactivate enveloped viruses at low pH.

In this experiment, the viral inactivation process was performed at 15 to 25° C. In a clean booth, the pH of the neutralized eluate from the affinity chromatography was adjusted to a pH of 3.0 to 3.8 (control pH 1), which is a reference pH, by adding a pH adjusting solution (0.1 M HCl) while stirring the eluate, and viral inactivation was performed at 18 to 24° C. for 45 minutes to 105 minutes.

After completion of the viral inactivation, the resulting solution was adjusted again to pH 4.5 to 5.5 (control pH 2) with a pH adjusting solution. Thereafter, the pH-adjusted process solution was filtered using a sterile capsule filter into a filtrate collection bag. After completion of the filtration, the virus-inactivated solution was subjected to a first ultrafiltration and diafiltration process which is the next process. The process parameters and QA/PA of the viral inactivation process are shown in Table 3 below.

TABLE 3

| Unit process | Process parameters | Operating conditions |
| --- | --- | --- |
| Viral inactivation | Operating temperature (° C.) | 20 ± 5 |
| | Control pH 1 | 3.4 ± 0.4 |
| | Control pH 2 | 5.0 ± 0.5 |
| | Inactivation time (min) | 75 ± 30 |

| Unit process | QA/PA | Results |
| --- | --- | --- |
| Viral inactivation | Yield (%) | 96.8 |
| | Purity (monomer %) | 96.4 |
| | HCP content (ng/mg) | 1043.9 |
| | LPA content (ng/mg) | 1.9 |

4. First Ultrafiltration and Diafiltration

A first ultrafiltration and diafiltration process is intended to subject the virus-inactivated solution to ultrafiltration and diafiltration under the load conditions of a first mixed-mode chromatography process.

The actual process was performed as follows.

An UF holder was equipped with a membrane and tightened with a torque wrench to a predetermined pressure so that a fixing plate is pressed. The assembled UF holder was named "UF system". The UF system was subjected to CIP by circulation with a first ultrafiltration and diafiltration CIP solution and flushed with water for injection and a first ultrafiltration and diafiltration buffer to stabilize the pH.

Thereafter, the TMP pressure was adjusted to 1.0±0.5 bar by adjusting a permeate valve and a retentate valve. The virus-inactivated solution was concentrated to 10±5 mg/mL and diafiltered with equilibration buffer (first ultrafiltration and diafiltration buffer) corresponding to 5 to 15 times the concentrated volume, and then whether the pH and conductivity would meet standards was checked and the diafiltration was terminated.

Thereafter, a 0.22 μm filter was connected to the retentate line, and post-washing was performed simultaneously with filtration. Then, the permeate valve was closed, and diafiltration buffer corresponding to about 10 to 30 vol % of the final retentate mass was injected into the feed line to pressurize the liquid stagnant in the concentrator and the feed line, and first post-washing was performed without drainage.

Diafiltration buffer corresponding to 20 to 40 vol % of the final retentate mass was injected into the feed line and circulated for 1 minute, and then second post-washing was performed while the rinse solution was completely discharged, thereby adjusting the retentate concentration to the final target concentration (3 to 7 mg/mL). Thereafter, the filtered first UF retentate was weighed, and recording paper was attached. The process parameters and QA/PA of the first ultrafiltration and diafiltration process performed as described above are shown in Table 4 below.

TABLE 4

| Unit process | Process parameters | Operating conditions |
| --- | --- | --- |
| First ultrafiltration and diafiltration | IMP (bar) | 1.0 ± 0.5 |
| | Target protein concentration (mg/mL) after ultrafiltration | 10 ± 5 |
| | pH after diafiltration | 4.6 ± 0.5 |
| | Diafiltration volume (folds) | 10 ± 5 |
| | Final target protein concentration (mg/mL) | 5 ± 2 |
| | Post-washing volume | First: 10 to 30% of final retentate mass<br>Second: 20 to 40% of final retentate mass |

| Unit process | QA/PA | Results |
| --- | --- | --- |
| First ultrafiltration and diafiltration | Yield (%) | 93.1 |
| | Purity (monomer %) | 96.3 |
| | HCP content (ng/mg) | 1054.5 |
| | LPA content (ng/mg) | 1.9 |

5. First Mixed-Mode Chromatography

A first mixed-mode chromatography process is intended to remove impurities such as HCP and LPA and increase purity.

The first mixed-mode chromatography purification process was performed using PPA mixed-mode resin at 15 to 25° C. First, packing evaluation was performed using an AKTA purification system to confirm suitability. Thereafter, a sterilization process was performed by flushing with CIP solution and passing column wash buffer through the column, and then an equilibration process was performed by flushing with equilibration buffer.

After equilibration was completed through the above-described processes, the first UF retentate was connected, and then a flow-through process was performed. For first mixed-mode chromatography purification, a sample was loaded in a flow-through mode process, and collection of the flow-through solution was started from the time point of loading. After completion of the sample loading, equilibration buffer was injected and a re-equilibration process was performed to completely recover the flow-through solution remaining in the column.

Thereafter, column washing was performed by flushing with column wash buffer, and column CIP was performed with CIP buffer. After completion of the CIP, the pH of the column was stabilized by flushing with equilibration buffer. Meanwhile, the column was filled with gel storage solution, and then separated from the system and stored separately.

The process parameters and QA/PA of the first mixed-mode chromatography process performed as described above are shown in Table 5 below.

TABLE 5

| Unit process | Process parameters | Operating conditions |
| --- | --- | --- |
| First mixed-mode chromatography | Operating pH | pH 4.6 ± 0.5 |
| | Sample loading concentration (mg/mL) | 5 ± 2 |
| | Amount of sample loaded (g/L of resin) | 40 ± 20 |

TABLE 5-continued

| Unit process | QA/PA | Results |
|---|---|---|
| First mixed-mode chromatography | Yield (%) | 99.5 |
| | Purity (monomer %) | 97.5 |
| | HCP content (ng/mg) | 87.4 |
| | HCP (LRV) | 1.1 |
| | LPA content (ng/mg) | 0.5 |
| | Endotoxin (EU/mg) | 0.13 |

6. Second Mixed-Mode Chromatography

This process is intended to remove a polymeric antibody and the remaining impurities such as HCP.

The second mixed-mode chromatography purification process was performed using CHT ceramic hydroxyapatite resin at 15 to 25° C. First, packing evaluation was performed using an AKTA purification system to confirm suitability.

Thereafter, the first mixed-mode chromatography flow-through solution was diluted at a ratio of 1:1 with dilution buffer and checked for it would meet pH and conductivity standards. It was used as loading solution after sterilization and filtration. Then, sterilization was performed by flushing with CIP 1 solution and passing column wash buffer through the column, and equilibration was performed by flushing with equilibration buffer. After completion of the equilibration as described above, a second mixed-mode chromatography loading solution was connected and an adsorption process was performed. After completion of the adsorption, a re-equilibration process was performed by flushing with equilibration buffer.

After completion of the re-equilibration, the column was flushed with elution buffer, and the eluate was collected until the UV peak fell below 0.1 AU. At this time, when the UV peak did not meet the standard, elution buffer corresponding to two times the gel volume was additionally loaded so that the UV value met the standard.

Thereafter, column washing was performed by flushing with column wash buffer. After completion of the column washing process, column CIP was performed by loading solutions in the order of CIP 2→CIP 3→CIP 2→CIP 1. In addition, the column was filled by flushing with gel storage solution, and then separated from the system and stored. The collected eluate was weighed, and then filtered and stored at 15 to 25° C. until use in the next process. The process parameters and operating conditions of the second mixed-mode chromatography process are shown in Table 6 below.

TABLE 6

| Unit process | Process parameters | Operating conditions |
|---|---|---|
| Second mixed-mode chromatography | Amount of sample loaded (g/L of resin) | 20 to 40 |
| | Sample loading pH | pH 5.5 to 6.5 |
| | Sample loading conductivity (mS/cm) | 2.3 ± 1.0 |
| | Elution buffer ion concentration (mM) | 100 to 160 |
| | Elution buffer pH | pH 6.0 ± 0.5 |
| | Criterion for termination of eluate collection (AU) | <0.1 |

| Unit process | QA/PA | Results |
|---|---|---|
| Second mixed-mode chromatography | Yield (%) | 94.3 |
| | Purity (monomer %) | 99.9 |
| | HCP content (ng/mg) | 13.2 |
| | HCP (LRV) | 0.8 |
| | LPA content (ng/mg) | 0.3 |

7. Second Ultrafiltration and Diafiltration

A second ultrafiltration and diafiltration process is intended to concentrate the second MM eluate to a target concentration and then diafilter the eluate with formulation buffer.

The UF system was subjected to CIP by circulation with a second ultrafiltration and diafiltration CIP solution, and flushed with water for injection and the second ultrafiltration and diafiltration buffer to stabilize the pH. In addition, the TMP pressure was adjusted to 1.0±0.5 bar by adjusting the permeate valve and the retentate valve.

Thereafter, the second mixed-mode chromatography eluate was concentrated to 20±5 mg/mL and diafiltered with equilibration buffer (second ultrafiltration and diafiltration buffer) corresponding to 5 to 15 times the concentrated volume. The pH and conductivity thereof were measured, and when they met the standards, the diafiltration was terminated.

In addition, the permeate valve was closed, a second ultrafiltration and diafiltration buffer corresponding to 10 to 30 vol % of the final retentate mass was injected into the feed line, and first post-washing was performed while transferring the liquid stagnant in the concentrator and the feed line without discharging the liquid.

Meanwhile, a second ultrafiltration and diafiltration buffer corresponding to 10 to 30 vol % of the final retentate mass was injected into the feed line and circulated for 1 minute, and then second post-washing was performed while completely discharging the rinse solution, thereby adjusting the retentate concentration to the target concentration (10 to 20 mg/mL).

Thereafter, a filter set of AIHC (Depth filter, Pre-filter) and Durapore 0.1 µm filter was connected to the second ultrafiltration and diafiltration retentate collection container, and filtration of the retentate was performed. After completion of the filtration, post-washing with a 3 to 7 L diafiltration buffer was performed, thereby adjusting the final concentration of the second ultrafiltration and diafiltration retentate to 5 to 15 mg/mL.

The second ultrafiltration and diafiltration retentate filtered as described above was weighed and stored at 15 to 25° C. until use in the next process. The process parameters and QA/PA of the second ultrafiltration and diafiltration process are shown in Table 7 below.

TABLE 7

| Unit process | Process parameters | Operating conditions |
|---|---|---|
| Second ultrafiltration and diafiltration | IMP | 1.0 ± 0.5 |
| | Target protein concentration (mg/mL) after ultrafiltration | 20 ± 5 |
| | Diafiltration volume (folds) | 10 ± 5 |
| | pH after diafiltration | 6.0 ± 0.5 |
| | Retentate target protein concentration (mg/mL) | 15 ± 5 |
| | Post-washing volume | Twice with 20 ± 10% of final retentate mass |
| | Filter post-washing volume (L) | 5 ± 2 |
| | Final target protein concentration (mg/mL) | 10 ± 5 |

| Unit process | QA/PA | Results |
|---|---|---|
| Second ultrafiltration and diafiltration | Yield (%) | 96.7 |
| | Purity (monomer %) | 99.9 |
| | HCP content (ng/mg) | 5.3 |
| | LPA content (ng/mg) | 0.4 |
| | Endotoxin (EU/mg) | 0.04 |

As can be seen from the above-described analysis result, the content of HCP in the anti-TFPI antibody composition obtained through the second ultrafiltration and diafiltration process was 5.3 ng/mg, the content of LPA in the anti-TFPI antibody composition was 0.4 ng/mg, and the total content of HCP and LPA was 5.7 ng/mg. The contents of HCP and LPA in the antibody composition were very low as described above, and thus it could be seen that the antibody composition could exhibit an excellent effect as an anti-TFPI antibody composition.

8. Nano-Filtration

A nano-filtration process is intended to remove viruses using a nano-filter.

The nano-filtration process was performed using a nano-filter (Viresolve Pro) at 15 to 25° C. First, the nano-filter was flushed with water for injection, and then washed with nano-filtration buffer. Thereafter, the pressure of the pressure regulator was adjusted to 2.0±0.5 bar, and the pressure valve was opened to initiate nano-filtration.

After completion of the nano-filtration, post-washing was performed with 1 to 3 L of nano-filtration buffer, and then the nano-filtrate was weighed. The process parameters and QA/PA of the nano-filtration process are shown in Table 8 below.

TABLE 8

| Unit process | Process parameters | Operating conditions |
| --- | --- | --- |
| Nano-filtration | Pressure (bar) | 2.0 ± 0.5 |
| | Post-washing volume (L) | 2 ± 1 |

| Unit process | QA/PA | Results |
| --- | --- | --- |
| Nano-filtration | Yield (%) | 98.0 |
| | Purity (monomer %) | 100.0 |
| | HCP content (ng/mg) | 4.5 |
| | LPA content (ng/mg) | 0.4 |

As can be seen from the above analysis results, the content of HCP in the anti-TFPI antibody composition obtained through the nano-filtration process was 4.5 ng/mg, the content of LPA in the antibody composition was 0.4 ng/mg, and the total content of HCP and LPA was 4.9 ng/mg. The contents of HCP and LPA were very low as described above, and thus it could be seen that the antibody composition could exhibit a very excellent effect as an anti-TFPI antibody composition.

9. Final Concentration

A final concentration process is intended to concentrate the nano-filtrate to the final target concentration. First, the permeate valve was opened, CIP was performed by circulation with final concentration CIP solution, and the pH was stabilized by flushing with water for injection and final concentration buffer.

Thereafter, the TMP pressure was adjusted to 1.0±0.5 bar by adjusting the permeate valve and the retentate valve, and the nano-filtrate was concentrated to 36±10 mg/mL. After completion of the concentration, additional concentration was performed up to 70% of the final mass, and then final concentration buffer corresponding to 10 vol % of the reduced 30% was injected and first post-washing was performed while transferring the liquid filled in the concentrate storage line without liquid leakage. In addition, final concentration buffer corresponding to the remaining 20 vol % was injected and circulated for 1 minute, and second post-washing was performed while completely discharging the rinse solution. The final concentrate was obtained and the mass thereof was measured. The process parameters and QA/PA of the final concentration process are shown in Table 9 below.

TABLE 9

| Unit process | Process parameters | Operating conditions |
| --- | --- | --- |
| Final concentration | TMP | 1.0 ± 0.5 bar (14.5 ± 7.2 psi) |
| | Final target concentration (mg/mL) | 36 ± 10 |
| | Post-washing volume (L) | First: once with 10% of final concentrate weight; second: once with 20% of final concentrate weight |

| Unit process | QA/PA | Results |
| --- | --- | --- |
| Final concentration | Yield (%) | 96.2 |
| | Purity (% monomer) | 100 |
| | HCP content (ng/mg) | 3.9 |
| | LPA content (ng/mg) | 0.5 |

As can be seen from the above analysis result, the content of HCP in the anti-TFPI antibody composition obtained through the final concentration process was 3.9 ng/mg, the content of LPA in the antibody composition was 0.5 ng/mg, and the total content of HCP and LPA was 4.4 ng/mg. The contents of HCP and LPA in the antibody composition were very low as described above, and thus it could be seen that the antibody composition could exhibit an excellent effect as an anti-TFPI antibody composition.

10. Drug Substance Formulation

A drug substance formulation process is intended to increase the stability of a drug substance by adding the excipient Polysorbate 80 and formulate the drug substance with a target concentration.

First, the excipient Polysorbate 80 was added to the final retentate and stirred for sufficient mixing, and the stirred solution was filtered through a 0.2 μm filter, thereby formulating a drug substance.

TABLE 10

| Unit process | Process parameters | Operating conditions |
| --- | --- | --- |
| Drug substance formulation | Final retentate volume (L) | 8 to 15 |
| | Amount of 5% Polysorbate 80 added (mL) | Final retentate amount/500 |
| | Stirring time (min) | 10 ± 5 |
| | Drug substance (kg) | 5 to 20 |

| Unit process | QA/PA | Results |
| --- | --- | --- |
| Drug substance formulation | Yield (%) | 95.7 |
| | Purity (% monomer) | 100.0 |
| | HCP content (ng/mg) | 4.1 |
| | LPA content (ng/mg) | 0.4 |
| | Binding activity potency | 1.91 |
| | $EC_{50}$ value (ng/mL) | |

As can be seen from the above analysis results, the content of HCP in the anti-TFPI antibody composition obtained through the drug substance formulation process was 4.1 ng/mg, the content of LPA in the antibody composition was 0.4 ng/mg, and the total content of HCP and LPA in the antibody composition was 4.5 ng/mg. The contents of HCP and LPA in the antibody composition were very low as described above, and thus it could be seen that the antibody composition could exhibit an excellent effect as an anti-TFPI antibody composition.

11. SDS-PAGE Analysis

Figure 1:
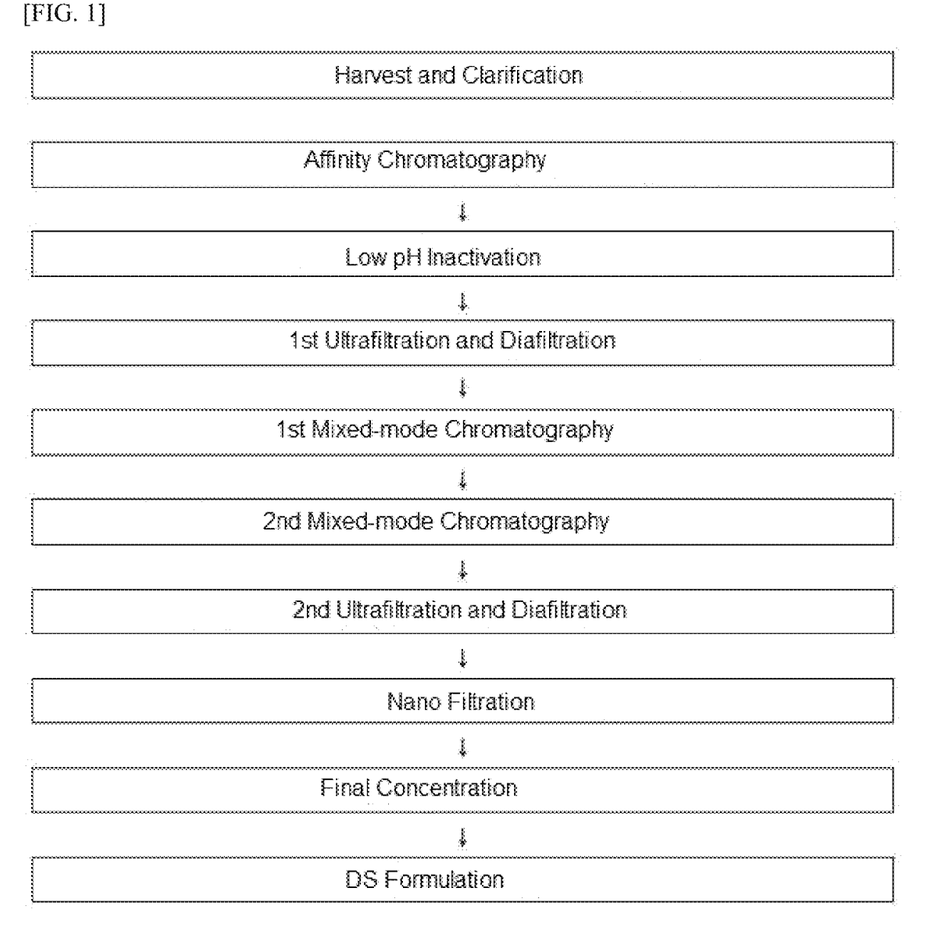
FIG. 1 schematically shows a flow chart of an overall process for producing a highly efficient anti-TFPI antibody composition of the present disclosure.
Figure 2A:
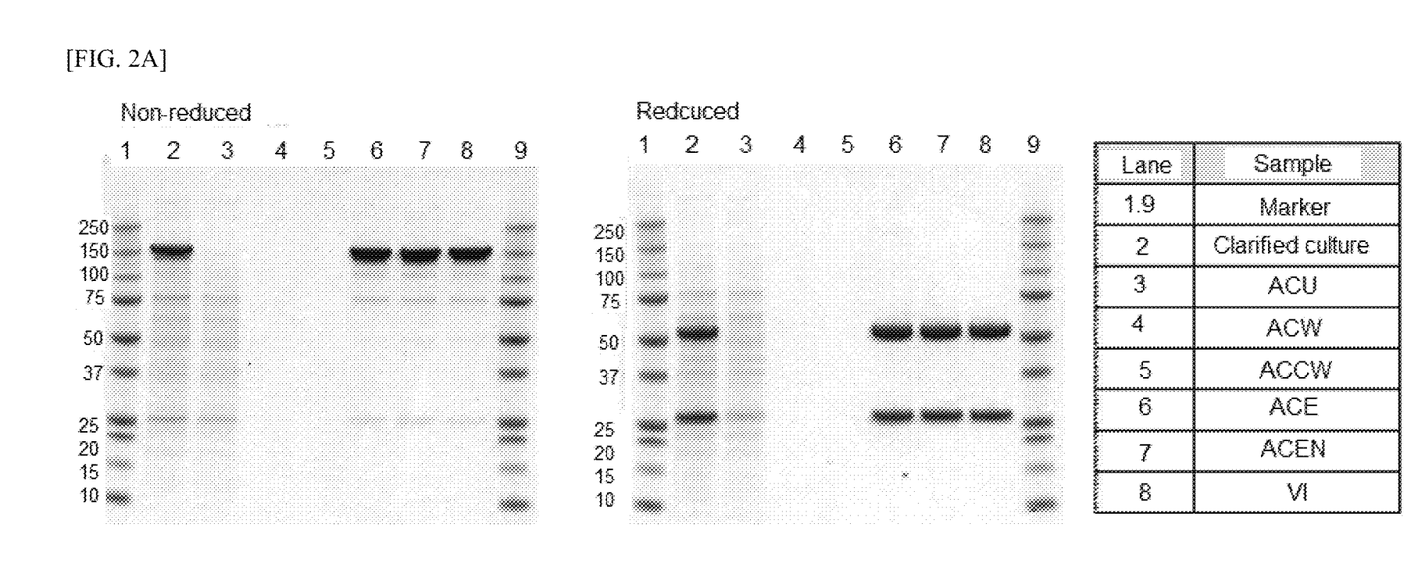
FIG. 2A shows the results of performing SDS-PAGE analysis on 150 kDa (which is the intrinsic size of the anti-TFPI antibody composition) under non-reduced conditions (left) and a 50 kDa heavy chain and a 25 kDa light chain under reduced conditions (right) in order to confirm an antibody in a substance in processes ranging from a culture harvest and clarification process to a viral inactivation process and to confirm an impurity removal pattern. The sample lanes of the shown SDS-PAGE gels are as follows: lanes 1 and 9—markers; lane 2—clarified culture; lane 3—affinity chromatography unbound solution (ACU); lane 4—affinity chromatography wash (ACW); lane 5—affinity chromatography column wash (ACCW); lane 6—affinity chromatography eluate (ACE); lane 7—affinity chromatography neutralized eluate (ACEN); lane 8—virus-inactivated solution (VI).
Figure 2B:
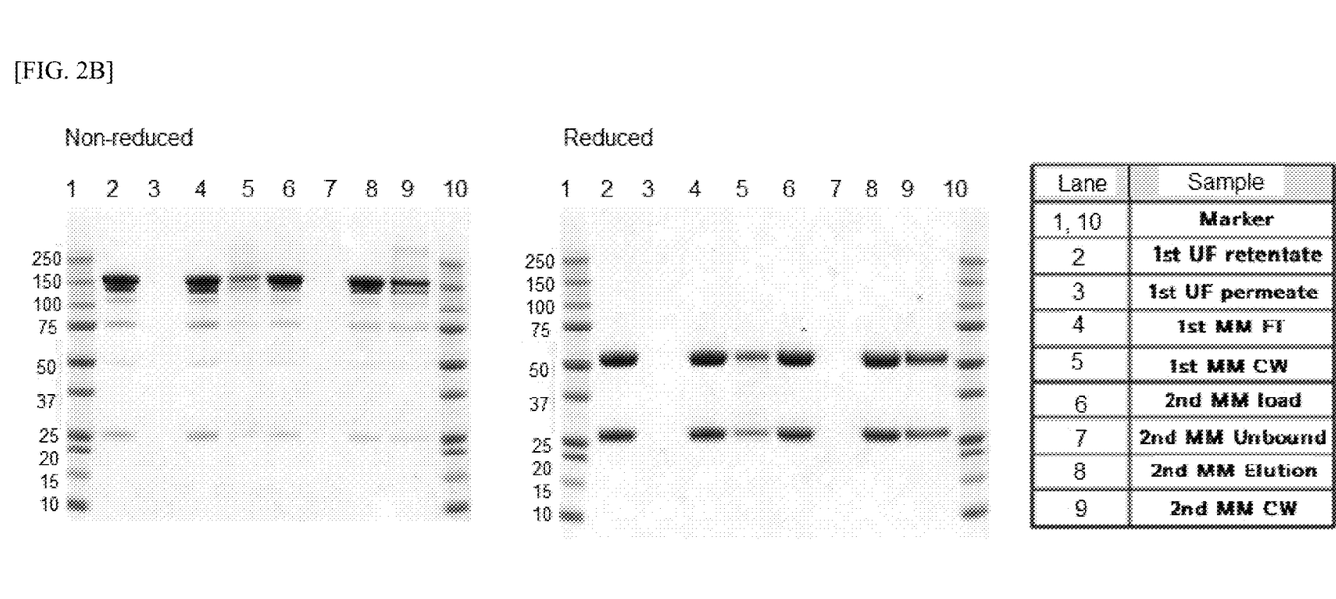
FIG. 2B shows the results of performing SDS-PAGE analysis on 150 kDa (which is the intrinsic size of the anti-TFPI antibody composition) under non-reduced conditions (left) and a 50 kDa heavy chain and a 25 kDa light chain under reduced conditions (right) in order to confirm an antibody in a substance in processes ranging from a first ultrafiltration and diafiltration process to a second mixed-mode chromatography process and to confirm an impurity removal pattern. The sample lanes of the shown SDS-PAGE gels are as follows: lanes 1 and 10—markers; lane 2—first UF retentate; lane 3—first UF permeate; lane 4—first mixed-mode flow-through solution ($1^{st}$ MM FT); lane 5—first mixed-mode column wash ($1^{st}$ MM CW); lane 6—second mixed-mode load solution ($2^{nd}$ MM Load); lane 7—second mixed-mode unbound solution ($2^{nd}$ MM unbound); lane 8—second mixed-mode eluate ($2^{nd}$ MM elution); lane 9—second mixed-mode column wash ($2^{nd}$ MM CW).
Figure 2C:
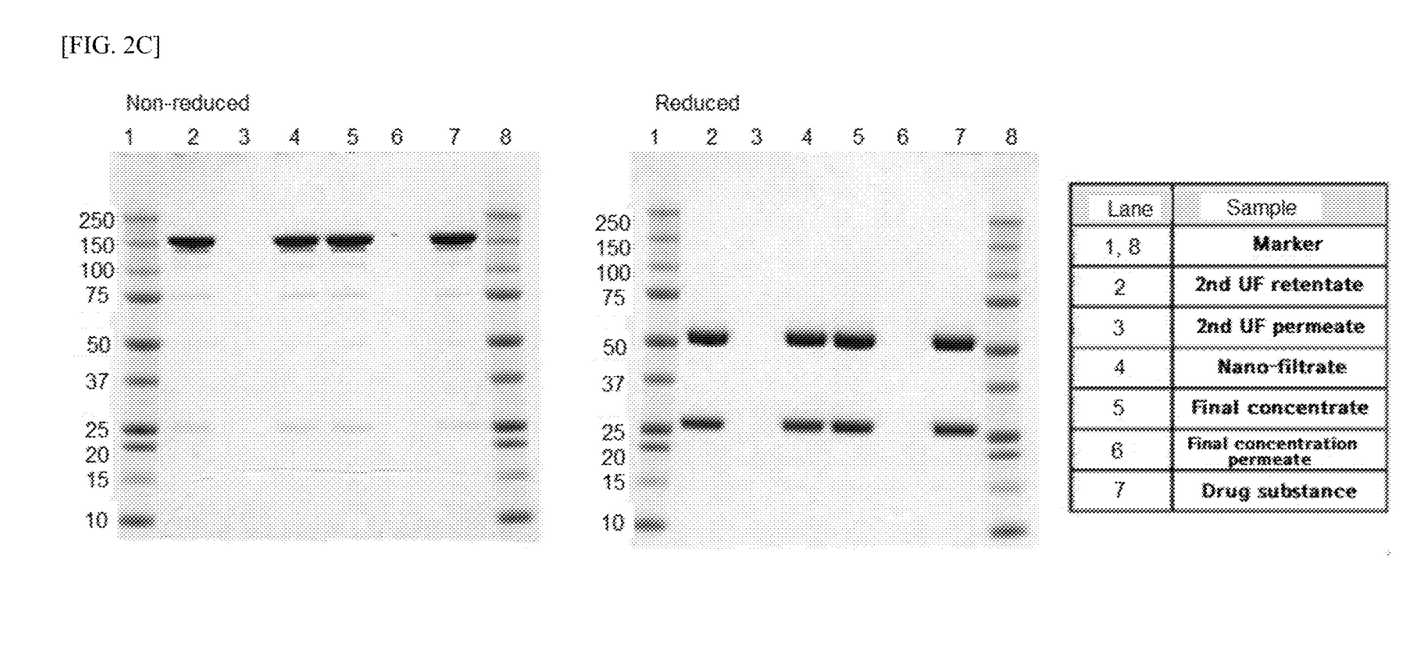
FIG. 2C shows the results of performing SDS-PAGE analysis on 150 kDa (which is the intrinsic size of the anti-TFPI antibody composition) under non-reduced conditions (left) and a 50 kDa heavy chain and a 25 kDa light chain under reduced conditions (right) in order to confirm an antibody in a substance in processes ranging from a second ultrafiltration and diafiltration process to a drug substance formulation process and to confirm an impurity removal pattern. The sample lanes of the shown SDS-PAGE gels are as follows: lanes 1 and 8—markers; lane 2—second UF retentate ($2^{nd}$ UF retentate); lane 3—second UF permeate ($2^{nd}$ UF permeate); lane 4—nanofiltrate; lane 5—final retentate; lane 6—final concentration permeate; lane 7—drug substance.

In order to confirm the antibody in the produced drug substance and confirm an impurity removal pattern, SDS-PAGE analysis was performed under reduced and non-reduced conditions.

In major samples from which the anti-TFPI antibody composition was purified during the process, the bands of 150 kDa (which is the intrinsic size of the antibody) under non-reduced conditions and a 50 kDa heavy chain and 25 kDa light chain under reduced conditions (FIGS. 2, 3 and 4) were considered as main bands. As a result, there was neither non-specific band occurrence nor impurity contamination. In addition, impurities were removed during the process, or the antibody bands were not detected as main bands in the unbound solution.

Therefore, it could be confirmed that the purification process of the present disclosure is an optimal process for effectively producing a highly efficient anti-TFPI antibody composition, which is not contaminated with impurities, microorganisms and viruses, from the raw material culture.

Hereinafter, the results of summarizing the results obtained by performing control experiments for the effect of the present disclosure will be described.

A. Process Optimization Experiment for Minimization of Polymer Generation

The present disclosure is characterized by minimizing polymer generation through introduction of a process of neutralizing an affinity chromatography eluate.

In order to minimize polymer generation, an anti-TFPI antibody composition was first eluted by maintaining the pH of the affinity chromatography elution process at 3.2 to 3.6. Next, viral inactivation was performed at low pH for 1 hour to 1 hour and 30 minutes to ensure viral stability, and then the next process was performed at increased pH. In order to confirm whether polymer generation can be minimized through introduction of the neutralization process, three control experiments were performed as follows.

Experimental Example 1

For a general antibody, viral inactivation was performed immediately after a low-pH affinity chromatography elution process, and in this case, the purity of the eluate from the elution process decreased from 96.0% to 85% after viral inactivation, and the polymer content thereof increased by 11%.

Experimental Example 2

After the low-pH affinity chromatography elution process, the eluate was left to stand at room temperature for 8 to 16 hours without pH adjustment, and then subjected to a viral inactivation process. In this case, a purity of 96% immediately after elution decreased to 83% after viral inactivation following 8 to 16 hours of standing, and the polymer content increased by 13%.

Experimental Example 3

After the low-pH affinity chromatography elution process, the eluate was neutralized to a pH of 4.8 to 5.2, left to stand at room temperature for 8 to 16 hours, and then titrated again to low pH and subjected to a viral inactivation process. In this case, a purity of 96% immediately after elution decreased to 91% after viral inactivation, and the polymer content increased by 5%.

Considering these Experimental Examples, it could be confirmed that the formation of the polymer was inhibited by about two times by stabilizing the substance through the pH neutralization process immediately after the affinity chromatography elution process and then performing the viral inactivation process.

The results of Experimental Examples 1 to 3 above are summarized in Table 11 below.

TABLE 11

|  | Experimental Example 1 | Experimental Example 2 | Experimental Example 3 |
|---|---|---|---|
| Affinity chromatography process (polymer concentration) | pH 3.8<br>7.447 mg/mL<br>96.02% | pH 3.8<br>7.447 mg/mL<br>96.02% | pH 3.8<br>7.447 mg/mL<br>96.02% |
| Neutralization process | — | — | pH 5.02<br>7.123 mg/mL<br>96.88% |
| Standing process | — | pH 3.8<br>7.447 mg/mL<br>98.44% | pH 5.02<br>7.094 mg/mL<br>96.87% |
| Viral inactivation process (polymer concentration) | pH 3.39 → 5.74<br>6.601 mg/mL<br>85.10% | pH 3.40 → 5.03<br>6.502 mg/mL<br>83.11% | pH 3.30 → 5.36<br>6.107 mg/mL<br>90.74% |

13. Examination of Correlation between Polymer Formation and Effect of Anti-TFPI Antibody In order to examine the correlation between polymer formation and the effect of the anti-TFPI antibody, anti-TFPI antibodies having monomer contents of 100%, 90% and 60%, respectively, were constructed by increasing polymer formation, and were tested for their binding activity potency.

The $EC_{50}$ value in the binding activity potency test for the anti-TFPI antibody composed of 100% monomer was determined to be 1.91 ng/mL. The $EC_{50}$ value in the binding activity potency test for the anti-TFPI antibody having a monomer purity of 90% due to an increased polymer content of 10% was determined to be 2.53 ng/mL. The $EC_{50}$ value in the binding activity potency test for the anti-TFPI antibody having a monomer purity of 60% due to an increased polymer content of 40% was determined to be 3.26 ng/mL. It was confirmed that as the polymer content increased, the binding activity of the antibody decreased, and that the binding activity potency value of the anti-TFPI antibody having a monomer purity of 60% decreased by 40% or more compared to the control having a monomer purity of 100%. The results are summarized in Table 12 below.

TABLE 12

| Samples | EC$_{50}$ (ng/mL) | Relative potency |
| --- | --- | --- |
| Monomer purity 100% | 1.91 | 100.0 |
| Monomer purity 90% | 2.53 | 75.5 |
| Monomer purity 60% | 3.26 | 58.6 |

B. Polymer Removal through CHT Resin

Anti-TFPI antibody is an IgG4 type antibody and has a higher rate of polymer generation than an IgG1 type antibody. As the polymer is generated, the binding affinity of the anti-TFPI antibody for TFPI decreases, and thus the effect of the antibody decreases. Hence, process conditions should be properly maintained to prevent the polymer from being generated in the production process. Nevertheless, a highly efficient antibody therapeutic agent can be developed only when a high-purity antibody sample can be produced by selectively removing the polymer produced in the intermediate process.

In order to selectively remove the polymer contained in the antibody during the process, the present inventors selected mixed-mode resin (which is the most efficient purification resin CHT ceramic hydroxyapatite) after screening and established optimal polymer separation conditions. As a result, it was confirmed that 12-23% polymer was removed through the purification process using CHT resin, and thus a purity close to 100% was obtained.

TABLE 13

| Column purification | Purity (%) Batch # | | |
| --- | --- | --- | --- |
| process using CHT resin | V7 | V8 | V9 |
| Loaded solution | 79.62 | 77.79 | 87.27 |
| Eluate | 100 | 100 | 99.97 |

C. Concentration and Buffer Circulation/Recovery Process

The recovery rate of the ultrafiltration and diafiltration process is influenced by pressure conditions, protein properties and protein concentration.

Therefore, it was confirmed that the recovery rate could be increased according to the protein recovery method under the same conditions. That is, it was confirmed that the yield could be increased by recovering even the protein adsorbed on the membrane while circulating the rinse solution.

The invention claimed is:

1. A method of preparing a pharmaceutical composition comprising a purified anti-tissue factor pathway inhibitor (anti-TFPI) antibody, wherein a content of host cell protein (HCP) in the composition is less than 10.0 ng/mg, and a content of leachable protein A (LPA) in the composition is less than 1.0 ng/mg,
wherein the anti-TFPI antibody is an IgG4 antibody,
the method comprising
(a) a step of clarifying a culture containing the anti-TFPI antibody to obtain a clarified culture, wherein the clarified culture is subjected to following (b)-(g), in this order;
(b) an affinity chromatography process at pH of 3.0 to 3.8, which further comprises the steps of:
(b-1) neutralizing an eluate, which passed through an affinity chromatography column, in the range of pH 4.0 to 6.0; and
(b-2) leaving the neutralized eluate obtained in (b-1) to stand at a temperature of 15 to 25° C. for 8 to 16 hours;
(c) a viral inactivation process;
(d) an ultrafiltration and diafiltration process;
(e) a mixed-mode chromatography process;
(f) a nano-filtration process; and
(g) a concentration process,
wherein the mixed-mode chromatography process (e) comprises performing two or more plural mixed-mode chromatography processes using different types of column resin to remove the anti-TFPI antibody in a form of polymer.

2. The method of claim 1, wherein a total content of the HCP and the LPA in the composition is 5 ng/mg or less.

3. The method of claim 1, wherein the mixed-mode chromatography process (e) removes 98% or more of the anti-TFPI antibody in a form of polymer.

4. The method of claim 1, wherein the concentration process comprises a rinse solution circulation/recovery process.

5. The method of claim 1, wherein a content of the anti-TFPI antibody in a form of polymer in the composition is less than 5%.

6. The method of claim 1, wherein a content of the anti-TFPI antibody in the composition, which is in a form of monomer, is greater than 60% based on a total amount of the anti-TFPI antibody contained in the composition.

7. The method of claim 1, wherein the HCP content in a composition obtained after a purification comprising (b)-(g) is at least 50,000-fold lower than the HCP content in the clarified culture obtained in (a) and before the purification.

8. The method of claim 1, wherein a relative potency value of the composition is 85% or higher compared to that of the composition in which 100% of the anti-TFPI antibody is in a form of monomer.

\* \* \* \* \*